United States Patent
Yanagida et al.

(10) Patent No.: US 12,329,545 B2
(45) Date of Patent: Jun. 17, 2025

(54) FILTERING APPARATUS, METHOD, PROGRAM, AND RECORDING MEDIUM

(71) Applicant: ADVANTEST CORPORATION, Tokyo (JP)

(72) Inventors: Tomonori Yanagida, Miyagi (JP); Yoshiyuki Hata, Miyagi (JP); Yuji Ogata, Miyagi (JP)

(73) Assignee: ADVANTEST CORPORATION, Tokyo (JP)

( * ) Notice: Subject to any disclaimer, the term of this patent is extended or adjusted under 35 U.S.C. 154(b) by 311 days.

(21) Appl. No.: 17/758,409

(22) PCT Filed: Feb. 5, 2021

(86) PCT No.: PCT/JP2021/004372
§ 371 (c)(1),
(2) Date: Jul. 6, 2022

(87) PCT Pub. No.: WO2021/181969
PCT Pub. Date: Sep. 16, 2021

(65) Prior Publication Data
US 2023/0018890 A1    Jan. 19, 2023

(30) Foreign Application Priority Data

Mar. 11, 2020  (JP) ................ 2020-042153

(51) Int. Cl.
*A61B 5/00* (2006.01)
*A61B 5/243* (2021.01)

(52) U.S. Cl.
CPC .............. *A61B 5/725* (2013.01); *A61B 5/243* (2021.01); *A61B 5/7203* (2013.01); *A61B 2562/0223* (2013.01)

(58) Field of Classification Search
CPC ....... A61B 5/725; A61B 5/243; A61B 5/7203; A61B 2562/0223; A61B 5/353;
(Continued)

(56) References Cited

U.S. PATENT DOCUMENTS 5,259,387 A * 11/1993 dePinto ................ H03H 17/06
                                                      600/521
9,986,951 B1 * 6/2018 Ferdosi ................ A61B 5/352
(Continued)

FOREIGN PATENT DOCUMENTS

JP    2006203613 A  *  8/2006
JP    2014-204220       10/2014
(Continued)

OTHER PUBLICATIONS

Mixed-Signal Design Seminar, 1991, Mixed-Signal Design Seminar, Edited by Walt Kester, section 7. (Year: 1991).*
(Continued)

*Primary Examiner* — Sophia Vlahos
(74) *Attorney, Agent, or Firm* — Greenblum & Bernstein, P.L.C.

(57) ABSTRACT

According to the present invention, a filtering apparatus includes an FIR filter that has multipliers arranged to multiply input digital data having their respective different input time points by respective variable tap coefficients. The variable tap coefficients are each switched from a first tap coefficient to a second tap coefficient sequentially for the input digital data from later to earlier input time points. The first tap coefficient is arranged to cause the FIR filter to serve as a low-pass filter with the cut-off frequency set at a first frequency. The second tap coefficient is arranged to cause the FIR filter to serve as a low-pass filter with the cut-off frequency set at a second frequency different from the first frequency.

14 Claims, 12 Drawing Sheets

(58) Field of Classification Search
CPC ......... A61B 5/355; A61B 5/366; A61B 5/358; A61B 5/36; H04L 25/0307; H04L 25/03019; H03H 21/001
See application file for complete search history.

(56) References Cited

U.S. PATENT DOCUMENTS

| | | | | |
|---|---|---|---|---|
| 2002/0151771 | A1* | 10/2002 | Braun | G16H 40/63 128/920 |
| 2006/0122525 | A1* | 6/2006 | Shusterman | A61B 5/411 600/513 |
| 2007/0176812 | A1* | 8/2007 | Inoue | H04B 3/23 341/144 |
| 2008/0027339 | A1 | 1/2008 | Nagai et al. | |
| 2009/0245342 | A1* | 10/2009 | Graffouliere | H04L 25/03038 375/232 |
| 2010/0100576 | A1* | 4/2010 | Willson, Jr. | H03H 17/0225 708/300 |
| 2013/0237874 | A1* | 9/2013 | Zoicas | A61B 5/7203 600/509 |
| 2017/0219661 | A1 | 8/2017 | Hata et al. | |
| 2018/0014738 | A1 | 1/2018 | Tanaka et al. | |
| 2019/0365266 | A1 | 12/2019 | Varcoe et al. | |

FOREIGN PATENT DOCUMENTS

| | | |
|---|---|---|
| JP | 2016-209019 | 12/2016 |
| JP | 2017-133993 | 8/2017 |
| JP | 2018-007821 | 1/2018 |
| JP | 2019-010483 | 1/2019 |
| WO | 2006/068145 | 6/2006 |
| WO | 2019/034841 | 2/2019 |

OTHER PUBLICATIONS

International Search Report (ISR) from International Searching Authority (Japan Patent Office) in International Pat. Appl. No. PCT/JP2021/004372, dated Apr. 13, 2021, together with an English language translation.

* cited by examiner $y[2] = a0x[2]+a1x[1]+a2x[0]$

FILTERING APPARATUS, METHOD, PROGRAM, AND RECORDING MEDIUM

TECHNICAL FIELD

The present invention relates to denoising magnetocardiographic and other measurement results.

BACKGROUND ART

There have conventionally been known electrocardiographic and magnetocardiographic measurements (see Patent Literatures 1, 2, and 3) and techniques for denoising magnetocardiographic measurement results as described in Patent Literatures 4 and 5.

CITATION LIST

Patent Literature

Patent Literature 1: WO2006/068145
Patent Literature 2: Japanese Patent Application Publication No. 2019-010483
Patent Literature 3: Japanese Patent Application Publication No. 2016-209019
Patent Literature 4: Japanese Patent Application Publication No. 2017-133993
Patent Literature 5: Japanese Patent Application Publication No. 2018-007821

SUMMARY OF THE INVENTION

Technical Problem

It is however difficult, even with such related arts as described above, to remove environmental noise by air-conditioning equipment or the like (e.g. air-conditioning noise) from magnetocardiographic measurement results.

This is for the reason that among magnetocardiographic measurement results (P-wave, QRS-wave, and T-wave), the P-wave and T-wave bands (0 to 10 Hz) do not overlap with the environmental noise band (20 Hz), while the QRS-wave band (0 to 50 Hz) overlaps with the environmental noise band (20 Hz). Thus, simply passing magnetocardiographic measurement results through a low-pass filter with the environmental noise band (20 Hz) set as a cut-off frequency could result in a significant attenuation of the QRS-wave.

To address this, it is necessary to smoothly switch the characteristics of the low-pass filter through which magnetocardiographic measurement results are passed. It is necessary, for example, to set the cut-off frequency at 20 Hz during P-wave input, thereafter switch the cut-off frequency to 50 Hz during QRS-wave input, and further switch the cut-off frequency back to 20 Hz during T-wave input.

It is hence an object of the present invention to smoothly switch the characteristics of a low-pass filter during denoising (e.g. removal of environmental noise from magnetocardiographic and other measurement results).

Means for Solving the Problem

According to the present invention, a filtering apparatus includes an FIR filter that has multipliers arranged to multiply input digital data having their respective different input time points by respective variable tap coefficients, wherein the variable tap coefficients are each switched from a first tap coefficient to a second tap coefficient sequentially for the input digital data from later to earlier input time points, the first tap coefficient is arranged to cause the FIR filter to serve as a low-pass filter with the cut-off frequency set at a first frequency, and the second tap coefficient is arranged to cause the FIR filter to serve as a low-pass filter with the cut-off frequency set at a second frequency different from the first frequency.

The thus constructed filtering apparatus includes an FIR filter that has multipliers arranged to multiply input digital data having their respective different input time points by respective variable tap coefficients. The variable tap coefficients are each switched from a first tap coefficient to a second tap coefficient sequentially for the input digital data from later to earlier input time points. The first tap coefficient is arranged to cause the FIR filter to serve as a low-pass filter with the cut-off frequency set at a first frequency. The second tap coefficient is arranged to cause the FIR filter to serve as a low-pass filter with the cut-off frequency set at a second frequency different from the first frequency.

According to the filtering apparatus of the present invention, the variable tap coefficients may be switched for each multiplication by one of the multipliers.

According to the present invention, the filtering apparatus may further include a delay summing section arranged to sum outputs from the multipliers while delaying to the input time point of the latest input digital data.

According to the filtering apparatus of the present invention, the variable tap coefficients may be recorded in the respective multipliers, and the variable tap coefficients recorded in the respective multipliers may be each switched completely from the first tap coefficient to the second tap coefficient at a predetermined time point.

According to the present invention, the filtering apparatus may further include: a delaying section arranged to delay inputs into the multipliers to the input time point of the latest input digital data; and a summing section arranged to sum outputs from the multipliers.

According to the filtering apparatus of the present invention, the first frequency may be lower than the second frequency.

According to the filtering apparatus of the present invention, the input digital data may include data representing magnetocardiographic P-wave and QRS-wave.

According to the filtering apparatus of the present invention, the variable tap coefficients may start to be switched at the time point when the QRS-wave starts in the magnetocardiographic waveform.

According to the filtering apparatus of the present invention, the input digital data may be acquired by a plurality of magnetocardiographic sensors, and the QRS-wave may start at the time point when the square average of the differences between outputs from the plurality of magnetocardiographic sensors and the average value thereof reaches the first local minimum value in the vicinity of the QRS-wave.

According to the filtering apparatus of the present invention, the first frequency may be higher than the second frequency.

According to the filtering apparatus of the present invention, the input digital data may include data representing magnetocardiographic P-wave, QRS-wave, and T-wave.

According to the filtering apparatus of the present invention, the variable tap coefficients may start to be switched at the time point when the QRS-wave ends in the magnetocardiographic waveform.

According to the filtering apparatus of the present invention, the input digital data may be acquired by a plurality of magnetocardiographic sensors, and the QRS-wave may end at the time point when the square average of the differences between outputs from the plurality of magnetocardiographic sensors and the average value thereof reaches the second local minimum value in the vicinity of the QRS-wave.

According to the present invention, a filtering method with using an FIR filter that has multipliers arranged to multiply input digital data having their respective different input time points by respective variable tap coefficients, includes switching the respective variable tap coefficients from a first tap coefficient to a second tap coefficient sequentially for the input digital data from later to earlier input time points, wherein the first tap coefficient is arranged to cause the FIR filter to serve as a low-pass filter with the cut-off frequency set at a first frequency, and the second tap coefficient is arranged to cause the FIR filter to serve as a low-pass filter with the cut-off frequency set at a second frequency different from the first frequency.

The present invention is a program of instructions for execution by a computer to perform a filtering process with using an FIR filter that has multipliers arranged to multiply input digital data having their respective different input time points by respective variable tap coefficients, the filtering process including switching the respective variable tap coefficients from a first tap coefficient to a second tap coefficient sequentially for the input digital data from later to earlier input time points, wherein the first tap coefficient is arranged to cause the FIR filter to serve as a low-pass filter with the cut-off frequency set at a first frequency, and the second tap coefficient is arranged to cause the FIR filter to serve as a low-pass filter with the cut-off frequency set at a second frequency different from the first frequency.

The present invention is a non-transitory computer-readable medium including a program of instructions for execution by a computer to perform a filtering process with using an FIR filter that has multipliers arranged to multiply input digital data having their respective different input time points by respective variable tap coefficients, the filtering process including switching the respective variable tap coefficients from a first tap coefficient to a second tap coefficient sequentially for the input digital data from later to earlier input time points, wherein the first tap coefficient is arranged to cause the FIR filter to serve as a low-pass filter with the cut-off frequency set at a first frequency, and the second tap coefficient is arranged to cause the FIR filter to serve as a low-pass filter with the cut-off frequency set at a second frequency different from the first frequency.

MODES FOR CARRYING OUT THE INVENTION

A description will now be given of embodiments of the present invention referring to drawings.

First Embodiment

Figure 1:
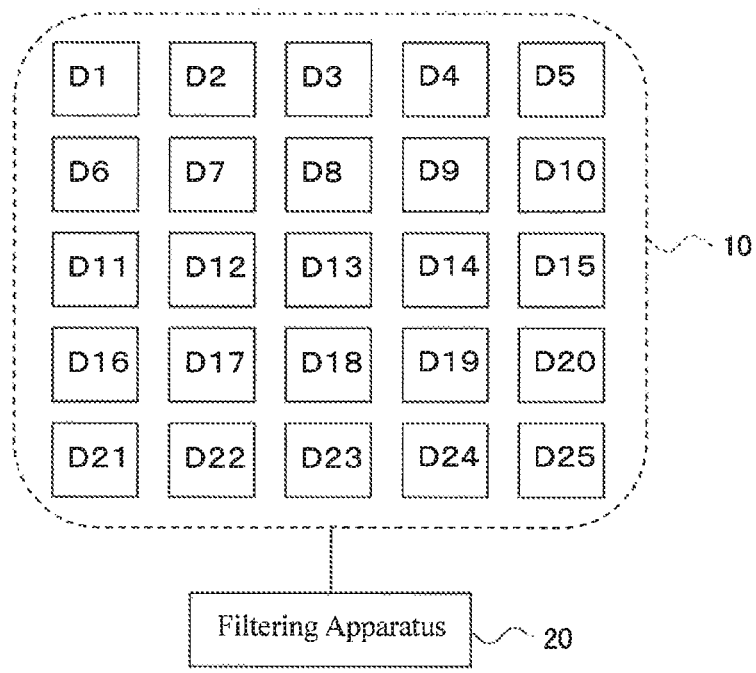
FIG. 1 is a functional block diagram showing the configuration of a magnetic measuring apparatus according to a first embodiment.

FIG. 1 is a functional block diagram showing the configuration of a magnetic measuring apparatus according to a first embodiment. The magnetic measuring apparatus (e.g. magnetocardiographic meter) according to the first embodiment includes a magnetic sensor group 10 and a filtering apparatus 20.

The magnetic sensor group 10 has magnetic sensors D1 to D25. The magnetic sensors D1 to D25 are magnetic measuring digital sensors arranged to output the magnetic flux density [pT] correspondingly to the sampling order n (=0, 1, 2, ... ) by the magnetic sensors D1 to D25. It is noted that since the sampling time point [ms]=(sampling period)×n, there is a correspondence between the sampling time point and n. It can therefore be said that the magnetic sensors D1 to D25 output the magnetic flux density [pT], as a measurement result, correspondingly to the sampling time point. In addition, the sampling order n is used as the sampling time point for the purpose of illustration because the sampling time point can be derived uniquely from the sampling order n.

It is noted that the magnetic sensors D1 to D25 are arranged in 5 rows×5 columns. D1, D2, ... , D5 are arranged in the first row. D6, D7, ... , D10 are arranged in the second row. D11, D12, ... , D15 are arranged in the third row. D16, D17, ... , D20 are arranged in the fourth row. D21, D22, ... , D25 are arranged in the fifth row. It is noted that the number and arrangement of the magnetic sensors is merely an example. For example, 64 magnetic sensors may be arranged in 8 rows×8 columns.

In addition, the measurement results by the magnetic sensors D1 to D25, which correspond to the sampling order (sampling time points) n, are represented as D1(n), D2(n), D24(n), D25(n).

The magnetic sensor group 10 is attached to, for example, the subject's chest. In this case, the magnetic sensors D1 to D25 are magnetocardiographic sensors arranged to detect the magnetic field from the heart.

The filtering apparatus 20 is arranged to receive the measurement results from the respective magnetic sensors D1 to D25 and filter out environmental noise (e.g. air-conditioning noise) for output.

Figure 2:
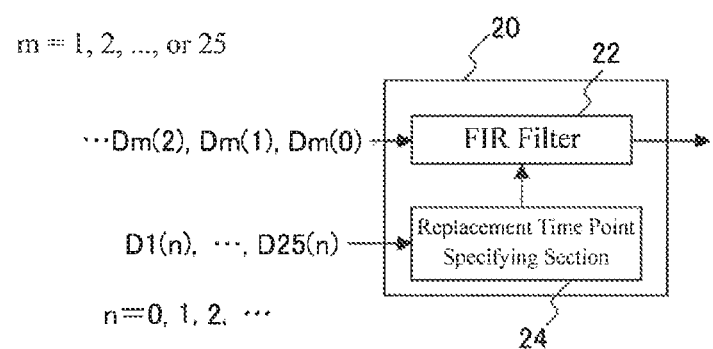
FIG. 2 is a functional block diagram showing the configuration of the filtering apparatus 20.

FIG. 2 is a functional block diagram showing the configuration of the filtering apparatus 20. The filtering apparatus 20 includes an FIR filter 22 and a replacement time point specifying section 24.

Figure 3:
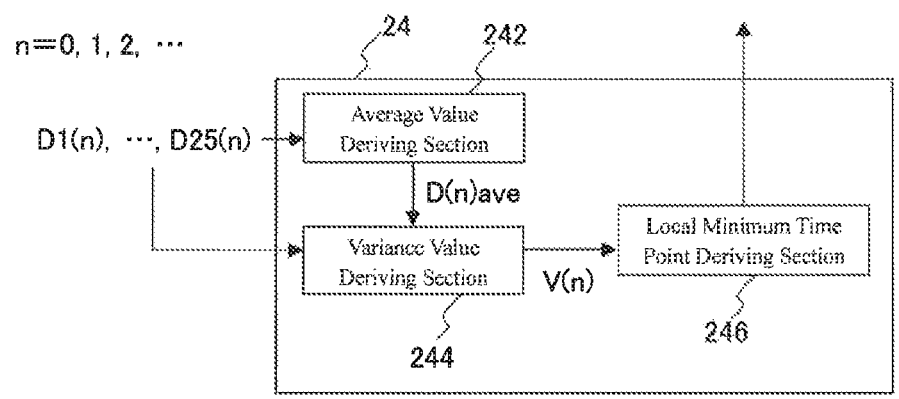
FIG. 3 is a functional block diagram showing the configuration of the replacement time point specifying section 24.

FIG. 3 is a functional block diagram showing the configuration of the replacement time point specifying section 24. The replacement time point specifying section 24 has an average value deriving section 242, a variance value deriving section 244, and a local minimum time point deriving section 246.

The measurement results D1($n$), D2($n$), D24($n$), D25($n$) acquired by the multiple magnetocardiographic sensors D1 to D25 are referred to as input digital data. The multiple magnetocardiographic sensors D1 to D25 are arranged to output the measurement results D1($n$), D2($n$), D24($n$), D25($n$).

The average value deriving section 242 is arranged to receive outputs from the multiple magnetocardiographic sensors D1 to D25 and output the average value D(n)ave of the outputs D1($n$) to D25($n$) from the multiple magnetocardiographic sensors. The average value D(n)ave is obtained by the following formula (1).

$$D(n)\text{ave}=(1/25)\times(D1(n)+D2(n)+\ldots+D24(n)+D25(n)) \quad (1)$$

The variance value deriving section 244 is arranged to receive outputs D1($n$) to D25($n$) from the multiple magnetocardiographic sensors D1 to D25 and further receive the average value D(n)ave from the average value deriving section 242. The variance value deriving section 244 is further arranged to derive the square average (i.e. variance value V(n)) of the differences between the outputs D1($n$) to D25($n$) from the multiple magnetocardiographic sensors D1 to D25 and the average value D(n)ave thereof. The square average (variance value V(n)) is obtained by the following formula (2). That is, the variance value V(n) is the square average of Dp(n)−D(n)ave (where p=1, 2, . . . , 24, 25).

$$V(n)=(1/25)\times((D1(n)-D(n)\text{ave})^2+(D2(n)-D(n)\text{ave})^2+\ldots+(D24(n)-D(n)\text{ave})^2+(D25(n)-D(n)\text{ave})^2) \quad (2)$$

The local minimum time point deriving section 246 is arranged to derive the time point when the variance value V(n) reaches a local minimum.

Figure 4:
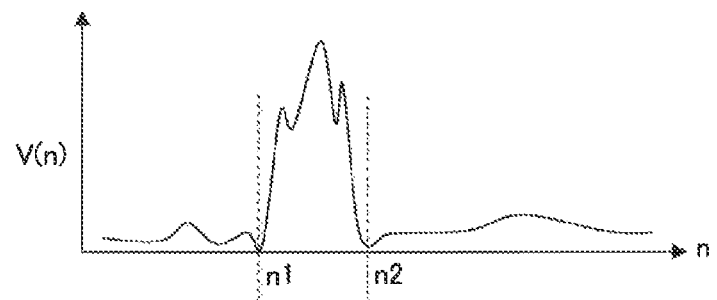
FIGS. 4 (a) and 4 (b) are graphs showing the correspondence between the variance value V(n) and the sampling time point n (FIG. 4 (a)) and the correspondence between the output from one of the magnetocardiographic sensors D1 to D25 and the sampling time point n (FIG. 4 (b))
Figure 4:
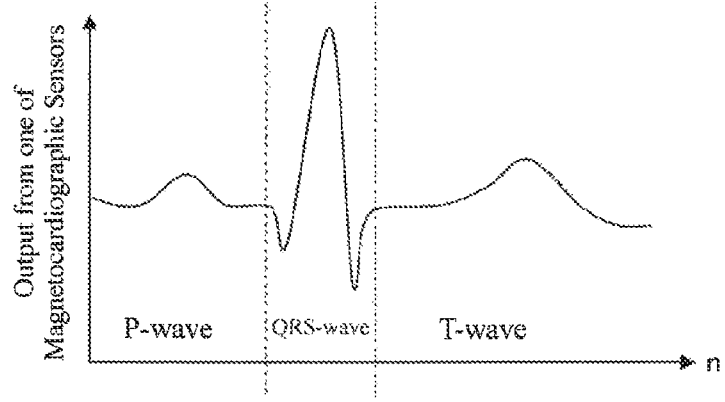

FIG. 4 is a graph showing the correspondence between the variance value V(n) and the sampling time point n (FIG. 4 (*a*)) and the correspondence between the output from one of the magnetocardiographic sensors D1 to D25 and the sampling time point n (FIG. 4 (*b*)).

Referring to FIG. 4 (*b*), the input digital data include data representing magnetocardiographic P-wave, QRS-wave, and T-wave. Note here that FIG. 4 (*b*) illustrates the output from one of the magnetocardiographic sensors D1 to D25 among the input digital data.

Referring to FIG. 4 (*a*), the time point when the variance value V(n) reaches the first local minimum in the vicinity of QRS-wave is set as n1. The time point when the variance value V(n) reaches the second local minimum in the vicinity of QRS-wave is set as n2.

Referring to FIGS. 4 (*a*) and 4 (*b*), the QRS-wave starts at the time point n1 when the variance value V(n) reaches the first local minimum.

The local minimum time point deriving section 246 of the replacement time point specifying section 24 is arranged to provide the time point n1 when the QRS-wave starts to the FIR filter 22.

Input digital data Dm(0), Dm(1), Dm(2), . . . are input to the FIR filter 22, where m=1, 2, . . . , or 25. For example, input digital data D1(0), D1(1), D1(2), . . . are input to the FIR filter 22. Note here that D2(0), D2(1), D2(2), . . . or D25(0), D25(1), D25(2), . . . may be input to the FIR filter 22.

The FIR filter 22 may be provided for each of the magnetic sensors D1 to D25 if needed. In this case, there are provided an FIR filter 22 to which input digital data D1(0), D1(1), D1(2), . . . are input, an FIR filter 22 to which input digital data D2(0), D2(1), D2(2), . . . are input, . . . , and an FIR filter 22 to which input digital data D25(0), D25(1), D25(2), . . . are input (25 FIR filters 22 are provided).

The input digital data may be considered to be sampled by the magnetic sensors D1 to D25 and, at the same time, provided to the FIR filter 22. It can therefore be said that the time point n when sampled by the magnetic sensors D1 to D25 is the time point (input time point) when input to the FIR filter 22.

Figure 5:
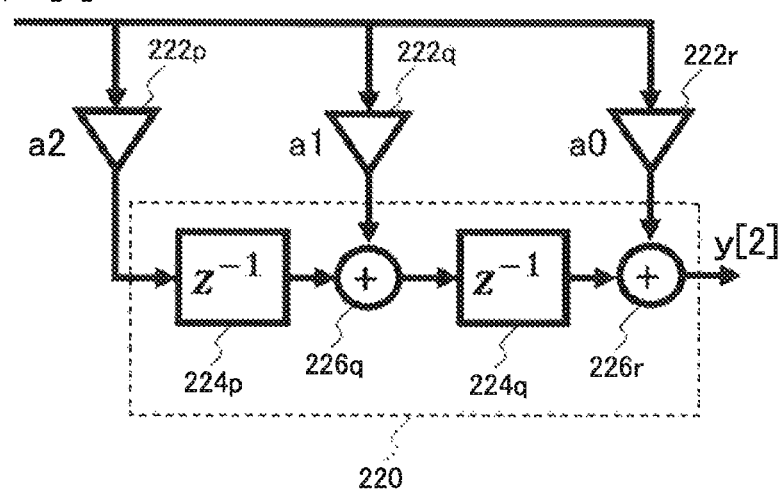
FIG. 5 shows the configuration of the FIR filter 22 at the input time point (sampling time point) n=2.
Figure 6:
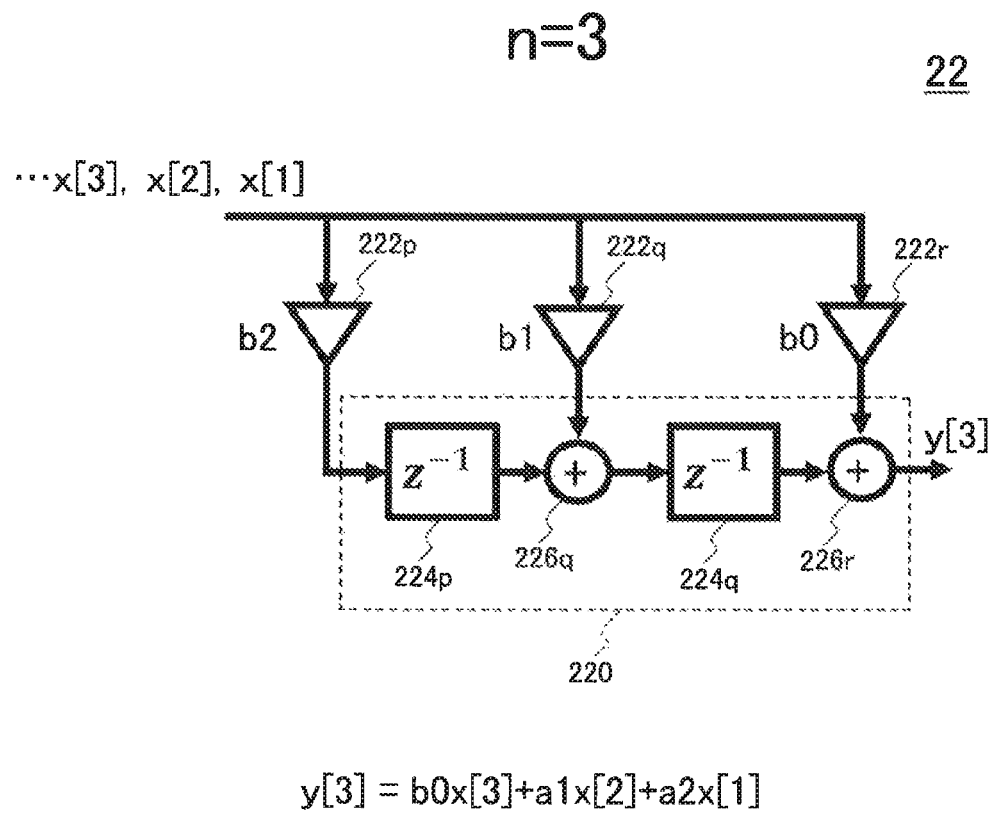
FIG. 6 shows the configuration of the FIR filter 22 at the input time point (sampling time point) n=3.
Figure 7:
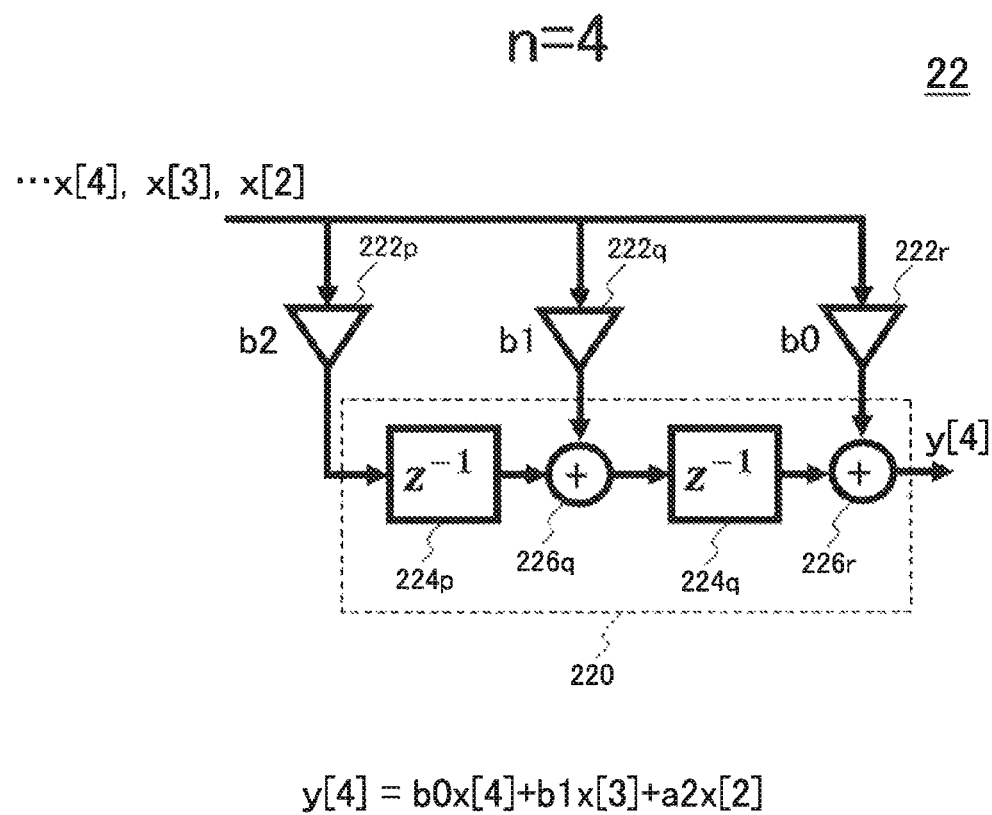
FIG. 7 shows the configuration of the FIR filter 22 at the input time point (sampling time point) n=4.
Figure 8:
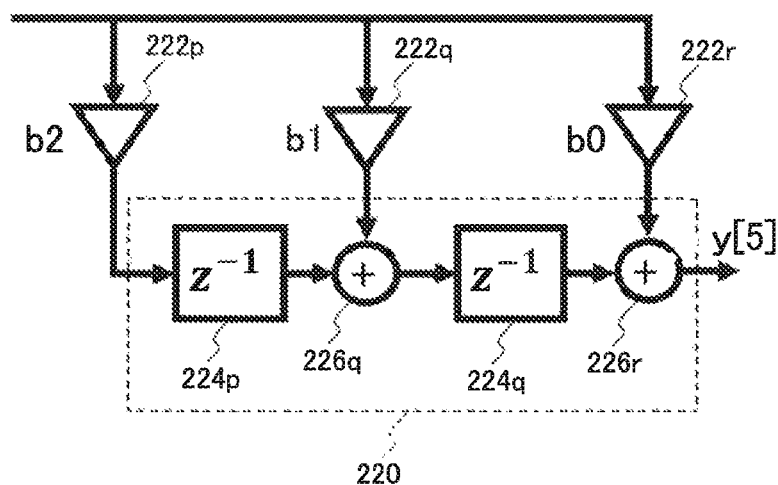
FIG. 8 shows the configuration of the FIR filter 22 at the input time point (sampling time point) n=5.

FIG. 5 shows the configuration of the FIR filter 22 at the input time point (sampling time point) n=2. FIG. 6 shows the configuration of the FIR filter 22 at the input time point (sampling time point) n=3. FIG. 7 shows the configuration of the FIR filter 22 at the input time point (sampling time point) n=4. FIG. 8 shows the configuration of the FIR filter 22 at the input time point (sampling time point) n=5.

Note here that in FIGS. 5 to 8, Dm(5), Dm(4), Dm(3), Dm(2), Dm(1), Dm(0) are represented as x[5], x[4], x[3], x[2], x[1], x[0] for the purpose of illustration. That is, Dm(n) is represented as x[n].

Referring to FIG. 5, the FIR filter 22 has a delay summing section 220 and multipliers 222*p*, 222*q*, 222*r*. The FIR filter 22 is a transposed FIR filter.

While input digital data x[2] is input to the FIR filter 22, input digital data x[1], x[0] that have not been processed through the FIR filter 22 are also processed.

The multipliers 222*p*, 222*q*, 222*r* are arranged to multiply input digital data x[0], x[1], x[2] having their respective different input time points n by respective variable tap coefficients. The variable tap coefficients have a0 (by which x[2] is multiplied), a1 (by which x[1] is multiplied), and a2 (by which x[0] is multiplied). The variable tap coefficients (a0, a1, a2) (first tap coefficients) are arranged to cause the FIR filter 22 to serve as a low-pass filter with the cut-off frequency set at a first frequency (20 Hz).

The FIR filter 22, if arranged to serve as a low-pass filter with the cut-off frequency set at a first frequency (20 Hz), is suited for cutting off environmental noise (e.g. 20 Hz component of air-conditioning noise) from magnetocardiographic P-wave (0 to 10 Hz) (see FIG. 4 (*b*)).

The delay summing section 220 has delayers 224*p*, 224*q* and adders 226*q*, 226*r*. The delayer 224*p* is arranged to delay the output from the multiplier 222*p* by time equal to one sampling period for output. The adder 226*q* is arranged to add the output from the delayer 224*p* and the output from the multiplier 222*q* for output. The delayer 224*q* is arranged to delay the output from the adder 226*q* by time equal to one sampling period for output. The adder 226*r* is arranged to add the output from the delayer 224*q* and the output from the multiplier 222*r* for output. The output from the adder 226*r* is the output y[n] from the FIR filter 22 (y[2] in FIG. 5).

The output (a2*x*[0]) from the multiplier 222*p* is delayed through the delayers 224*p* and 224*q* by time equal to two sampling periods to the input time point n (=2) of the latest input digital data x[2], while summed through the adders 226*q* and 226*r* with the outputs from the multipliers 222*q* and 222*r*.

The output (a1*x*[1]) from the multiplier 222*q* is delayed through the delayer 224*q* by time equal to one sampling period to the input time point n (=2) of the latest input digital data x[2], while summed through the adder 226*r* with the output from the multiplier 222*r*.

The delay summing section 220 is thus arranged to sum the outputs from the multipliers 222*p*, 222*q* while delaying to the input time point n (=2) of the latest input digital data x[2]. Accordingly, the FIR filter 22 outputs y[2]=a0*x*[2]+a1*x*[1]+a2*x*[0].

It is noted that referring to FIG. 8, the variable tap coefficients to which input digital data x[5], x[4], x[3] having their respective different input time points n are multiplied have b0 (by which x[5] is multiplied), b1 (by which x[4] is multiplied), and b2 (by which x[3] is multiplied). The variable tap coefficients (b0, b1, b2) (second tap coefficients) are arranged to cause the FIR filter 22 to serve as a low-pass filter with the cut-off frequency set at a second frequency (50 Hz).

It is noted that the first frequency (20 Hz) is lower than the second frequency (50 Hz).

The FIR filter 22, if arranged to serve as a low-pass filter with the cut-off frequency set at a second frequency (50 Hz), is suited for cutting off environmental noise (e.g. 20 Hz component of air-conditioning noise) from magnetocardiographic QRS-wave (0 to 50 Hz) (see FIG. 4 (*b*)).

However, switching the variable tap coefficients from the first tap coefficients (a0, a1, a2) to the second tap coefficients (b0, b1, b2) immediately when the QRS-wave starts may cause discontinuity between the P-wave and the QRS-wave in the output from the FIR filter 22.

Hence, the variable tap coefficients are switched gradually from the first tap coefficients (a0, a1, a2) to the second tap coefficients (b0, b1, b2) when the QRS-wave starts to smoothly switch the characteristics of the FIR filter 22 serving as a low-pass filter.

Here assume that the time point n1 when the QRS-wave starts is at the input time point n=3.

The variable tap coefficients start to be switched at the time point n=3 when the QRS-wave starts in the magnetocardiographic waveform (see FIG. 6).

The switching is under the following procedure: the variable tap coefficients are each switched from the first tap coefficient (a2, a1, a0) to the second tap coefficient (b2, b1, b0) sequentially for the input digital data from later to earlier input time points n. Note here that the variable tap coefficients are switched for each multiplication by the multiplier 222*r*.

First, the variable tap coefficients have the first tap coefficients (a2, a1, a0) at the input time point n=2 (see FIG. 5). Here, the variable tap coefficient by which the input digital data x[2] having the latest input time point n is multiplied has a0, the variable tap coefficient by which the next later input digital data x[1] is multiplied has a1, and the variable tap coefficient by which the earliest input digital data x[0] is multiplied has a2.

The first tap coefficients (a0, a1, a2) are thus switched in the order of a0, a1, and a2 to the second tap coefficients (b0, b1, b2). That is, the variable tap coefficients have (a0, a1, a2) (see FIG. 5), (b0, a1, a2) (see FIG. 6), (b0, b1, a2) (see FIG. 7), and (b0, b1, b2) (see FIG. 8) over time.

The variable tap coefficients have (a0, a1, a2) after multiplication by the multiplier 222*r* in FIG. 5 (at the time point n=2), the variable tap coefficients have (b0, a1, a2) after multiplication by the multiplier 222*r* in FIG. 6 (at the time point n=3), the variable tap coefficients have (b0, b1, a2) after multiplication by the multiplier 222*r* in FIG. 7 (at the time point n=4), and the variable tap coefficients have (b0, b1, b2) after multiplication by the multiplier 222*r* in FIG. 8 (at the time point n=5). The variable tap coefficients are thus switched for each multiplication by the multiplier 222*r*.

In order to achieve such variable tap coefficient switching, the variable tap coefficients are recorded in the respective multipliers 222*p*, 222*q*, 222*r*. Then, the variable tap coefficients recorded in the respective multipliers 222*p*, 222*q*, 222*r* are switched completely from the first tap coefficient (a2, a1, a0) to the second tap coefficient (b2, b1, b0) at a predetermined time point (e.g. at the time point n=3 when the QRS-wave starts).

Referring to FIG. 5, the variable tap coefficients have a2, a1, a0 at the time point n=2. Next, referring to FIG. 6, the variable tap coefficients recorded in the respective multipliers 222*p*, 222*q*, 222*r* are switched completely to b2, b1, b0 at the time point n=3. The multipliers 222*p*, 222*q*, 222*r* are arranged to multiply input digital data x[1], x[2], x[3] having their respective different input time points n by respective variable tap coefficients. Since multiplication by the multiplier 222*r* is performed at the time point n=3, the multiplier 222*r* outputs b0*x*[3]. However, since multiplication by the multipliers 222*p*, 222*q* is performed, respectively, at the time points n=1, 2, the variable tap coefficients have a2, a1. Accordingly, the multipliers 222*p*, 222*q* output a2*x*[1], a1*x*[2], respectively.

Accordingly, the FIR filter 22 outputs y[3]=b0*x*[3]+a1*x*[2]+a2*x*[1]. The variable tap coefficients then have (b0, a1, a2).

Next, referring to FIG. 7, the multipliers 222*p*, 222*q*, 222*r* are arranged to multiply input digital data x[2], x[3], x[4] having their respective different input time points n by respective variable tap coefficients. Since multiplication by the multiplier 222*r* is performed at the time point n=4, the multiplier 222*r* outputs b0*x*[4]. Since multiplication by the multiplier 222*q* is performed at the time point n=3, the multiplier 222*q* outputs b1*x*[3]. However, since multiplication by the multiplier 222*p* is performed at the time point n=2, the variable tap coefficient has a2. Accordingly, the multiplier 222*p* outputs a2*x*[2].

Accordingly, the FIR filter 22 outputs y[4]=b0*x*[4]+b1*x*[3]+a2*x*[2]. The variable tap coefficients then have (b0, b1, a2).

Finally, referring to FIG. 8, the multipliers 222*p*, 222*q*, 222*r* are arranged to multiply input digital data x[3], x[4], x[5] having their respective different input time points n by respective variable tap coefficients. Since multiplication by the multiplier 222*r* is performed at the time point n=5, the multiplier 222*r* outputs b0*x*[5]. Since multiplication by the multiplier 222*q* is performed at the time point n=4, the multiplier 222*q* outputs b1*x*[4]. Since multiplication by the multiplier 222*p* is performed at the time point n=3, the variable tap coefficient has b2. Accordingly, the multiplier 222*p* outputs b2*x*[3].

Accordingly, the FIR filter 22 outputs y[5]=b0*x*[5]+b1*x*[4]+b2*x*[3]. The variable tap coefficients then have (b0, b1, b2).

Next will be described an operation according to the first embodiment.

First, when the magnetic sensor group 10 (see FIG. 1) is attached to the subject's chest, the magnetic sensors D1 to D25 detect the magnetic field from the heart and output correspondingly to the sampling order n (=0, 1, 2, ... ) (input time points).

The outputs D1(*n*), D2(*n*), ... , D24(*n*), D25(*n*) from the magnetic sensors D1 to D25 are provided to the replacement time point specifying section 24 of the filtering apparatus 20. The replacement time point specifying section 24 provides the FIR filter 22 with the time point n1 (see FIG. 4) when the variance value V(n) reaches the first local minimum in the vicinity of QRS-wave. For example, n1 is at the input time point n=3. The QRS-wave starts at the time point n1.

The variable tap coefficients in the FIR filter 22 initially have the first tap coefficients (a0, a1, a2) (see FIG. 5), which are suited for cutting off environmental noise (e.g. 20 Hz component of air-conditioning noise) from magnetocardiographic P-wave (0 to 10 Hz) (see FIG. 4 (b)).

The variable tap coefficients recorded in the respective multipliers 222p, 222q, 222r are then switched completely from the first tap coefficient (a2, a1, a0) to the second tap coefficient (b2, b1, b0) at the time point n=3 (see FIG. 6).

The variable tap coefficients are then switched gradually from the first tap coefficient (a0, a1, a2) to the second tap coefficient (b0, b1, b2) such that the FIR filter 22 outputs y[3]=b0x[3]+a1x[2]+a2x[1] (variable tap coefficients b0, a1, a2; see FIG. 6), the FIR filter 22 outputs y[4]=b0x[4]+b1x[3]+a2x[2] (variable tap coefficients b0, b1, a2; see FIG. 7), and then the FIR filter 22 outputs y[5]=b0x[5]+b1x[4]+b2x[3] (variable tap coefficients b0, b1, b2; see FIG. 8).

The variable tap coefficients in the FIR filter 22 are thus switched to the second tap coefficients (b0, b1, b2) (see FIG. 8), which are suited for cutting off environmental noise (e.g. 20 Hz component of air-conditioning noise) from magnetocardiographic QRS-wave (0 to 50 Hz) (see FIG. 4 (b)).

In accordance with the first embodiment, it is possible to smoothly switch the characteristics of the low-pass filter (FIR filter 22) during denoising (e.g. removal of environmental noise from magnetocardiographic and other measurement results).

Variation

It is noted that the FIR filter 22 may not be a transposed FIR filter as long as the first tap coefficients (a0, a1, a2) can be switched in the order of a0, a1, and a2 to the second tap coefficients (b0, b1, b2), though has been described as a transposed FIR filter in the first embodiment. For example, the FIR filter 22 may be a direct FIR filter.

Figure 9:
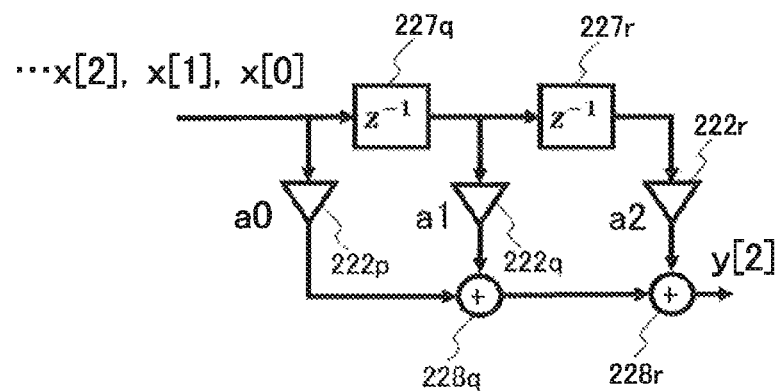
FIG. 9 shows the configuration of the FIR filter 22 at the input time point (sampling time point) n=2 according to a variation of the first embodiment.
Figure 10:
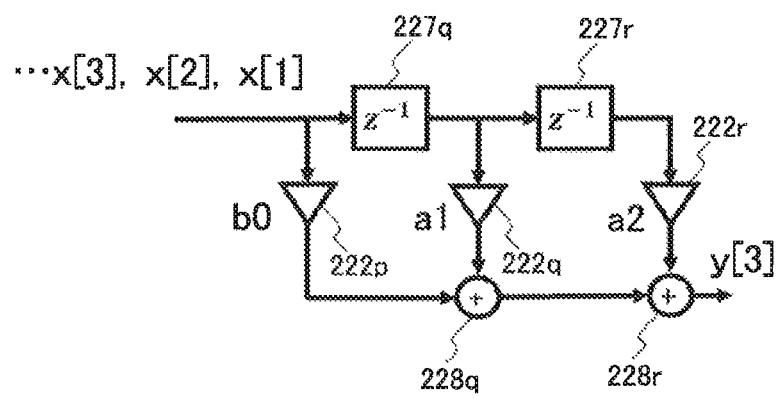
FIG. 10 shows the configuration of the FIR filter 22 at the input time point (sampling time point) n=3 according to the variation of the first embodiment.
Figure 11:
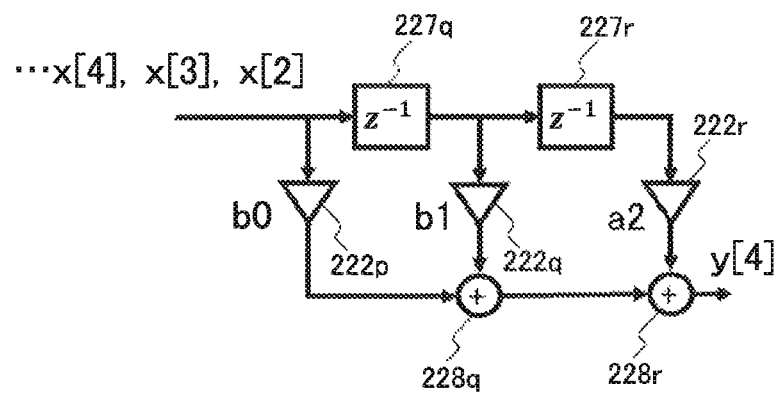
FIG. 11 shows the configuration of the FIR filter 22 at the input time point (sampling time point) n=4 according to the variation of the first embodiment.
Figure 12:
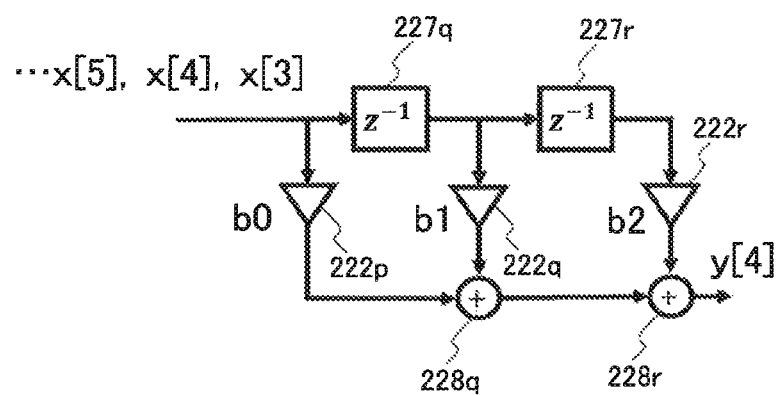
FIG. 12 shows the configuration of the FIR filter 22 at the input time point (sampling time point) n=5 according to the variation of the first embodiment.

FIG. 9 shows the configuration of the FIR filter 22 at the input time point (sampling time point) n=2 according to a variation of the first embodiment. FIG. 10 shows the configuration of the FIR filter 22 at the input time point (sampling time point) n=3 according to the variation of the first embodiment. FIG. 11 shows the configuration of the FIR filter 22 at the input time point (sampling time point) n=4 according to the variation of the first embodiment. FIG. 12 shows the configuration of the FIR filter 22 at the input time point (sampling time point) n=5 according to the variation of the first embodiment.

Referring to FIG. 9, the FIR filter 22 according to the variation of the first embodiment has delaying sections 227q, 227r, multipliers 222p, 222q, 222r, and adders 228q, 228r. The FIR filter 22 according to the variation of the first embodiment is a direct FIR filter.

The delaying section 227q is arranged to delay the input to the multiplier 222p by time equal to one sampling period for output. The delaying section 227r is arranged to delay the input to the multiplier 222q by time equal to one sampling period for output.

The adder 228q is arranged to add the output from the multiplier 222p and the output from the multiplier 222q for output. The adder 228r is arranged to add the output from the adder 228q and the output from the multiplier 222r for output. The adders 228q and 228r form a summing section arranged to sum outputs from the multipliers 222p, 222q, 222r.

The multipliers 222p, 222q, 222r are arranged to multiply input digital data x[2], x[1], x[0] having their respective different input time points n by respective variable tap coefficients a0, a1, a2.

The delaying section 227q is arranged to delay the input x[1] to the multiplier 222q by time equal to one sampling period to the input time point n (=2) of the latest input digital data x[2].

The delaying sections 227q and 227r are arranged to delay the input x[0] to the multiplier 222r by time equal to two sampling periods to the input time point n (=2) of the latest input digital data x[2].

Accordingly, the FIR filter 22 outputs y[2]=a0x[2]+a1x[1]+a2x[0].

Next, referring to FIG. 10, the variable tap coefficient a0 recorded in the multiplier 222p is switched to b0 at the time point n=3. The variable tap coefficients recorded in the respective multipliers 222q, 222r still remain a1, a2. The multipliers 222p, 222q, 222r are arranged to multiply input digital data x[3], x[2], x[1] having their respective different input time points n by respective variable tap coefficients.

Accordingly, the FIR filter 22 outputs y[3]=b0x[3]+a1x[2]+a2x[1]. The variable tap coefficients then have (b0, a1, a2).

Next, referring to FIG. 11, the variable tap coefficient a1 recorded in the multiplier 222q is switched to b1 at the time point n=4. The variable tap coefficient recorded in the multiplier 222r still remains a2. The multipliers 222p, 222q, 222r are arranged to multiply input digital data x[4], x[3], x[2] having their respective different input time points n by respective variable tap coefficients.

Accordingly, the FIR filter 22 outputs y[4]=b0x[4]+b1x[3]+a2x[2]. The variable tap coefficients then have (b0, b1, a2).

Finally, referring to FIG. 12, the variable tap coefficient a2 recorded in the multiplier 222r is switched to b2 at the time point n=5. The multipliers 222p, 222q, 222r are arranged to multiply input digital data x[5], x[4], x[3] having their respective different input time points n by respective variable tap coefficients.

Accordingly, the FIR filter 22 outputs y[5]=b0x[5]+b1x[4]+b2x[3]. The variable tap coefficients then have (b0, b1, b2).

Second Embodiment

In a second embodiment, the variable tap coefficients start to be switched when the QRS-wave ends, which is different from the first embodiment in which the variable tap coefficients start to be switched when the QRS-wave starts.

The configuration of the magnetic measuring apparatus according to the second embodiment is identical to that of the first embodiment and will not be described (see FIG. 1).

Since the configuration of the filtering apparatus 20 according to the second embodiment is almost the same as in the first embodiment (see FIGS. 2 and 3), the differences from the first embodiment will hereinafter be described.

The filtering apparatus 20 according to the second embodiment includes an FIR filter 22 and a replacement time point specifying section 24 (see FIG. 2). The replacement time point specifying section 24 has an average value deriving section 242, a variance value deriving section 244, and a local minimum time point deriving section 246 (see FIG. 3). The average value deriving section 242 and the variance value deriving section 244 are identical to those in the first embodiment and will not be described (see Formulae (1) and (2)).

The local minimum time point deriving section 246 is arranged to derive the time point when the variance value V(n) reaches a local minimum.

Referring to FIGS. 4 (a) and 4 (b), the QRS-wave ends at the time point n2 when the variance value V(n) reaches the second local minimum.

The local minimum time point deriving section 246 of the replacement time point specifying section 24 is arranged to provide the time point n2 when the QRS-wave ends to the FIR filter 22.

The configuration of the FIR filter 22 is identical to that of the first embodiment (see FIGS. 5 to 8). However, contrary to the first embodiment, the first frequency (50 Hz) is higher than the second frequency (20 Hz).

That is, the first tap coefficients (a0, a1, a2) are arranged to cause the FIR filter 22 to serve as a low-pass filter with the cut-off frequency set at a first frequency (50 Hz). The FIR filter 22, if arranged to serve as a low-pass filter with the cut-off frequency set at a first frequency (50 Hz), is suited for cutting off environmental noise (e.g. 20 Hz component of air-conditioning noise) from magnetocardiographic QRS-wave (0 to 50 Hz) (see FIG. 4 (b)).

On the other hand, the second tap coefficients (b0, b1, b2) are arranged to cause the FIR filter 22 to serve as a low-pass filter with the cut-off frequency set at a second frequency (20 Hz). The FIR filter 22, if arranged to serve as a low-pass filter with the cut-off frequency set at a second frequency (20 Hz), is suited for cutting off environmental noise (e.g. 20 Hz component of air-conditioning noise) from magnetocardiographic T-wave (0 to 10 Hz) (see FIG. 4 (b)).

Here assume that the time point n2 when the QRS-wave ends is at the input time point n=3. The variable tap coefficients start to be switched at the time point n=3 when the QRS-wave ends in the magnetocardiographic waveform (see FIG. 6). The procedure under which the variable tap coefficients are switched is identical to that of the first embodiment and will not be described.

Next will be described an operation according to the second embodiment.

First, when the magnetic sensor group 10 (see FIG. 1) is attached to the subject's chest, the magnetic sensors D1 to D25 detect the magnetic field from the heart and output correspondingly to the sampling order n (=0, 1, 2, . . . ) (input time points).

The outputs D1(n), D2(n), . . . , D24(n), D25(n) from the magnetic sensors D1 to D25 are provided to the replacement time point specifying section 24 of the filtering apparatus 20. The replacement time point specifying section 24 provides the FIR filter 22 with the time point n2 (see FIG. 4) when the variance value V(n) reaches the second local minimum in the vicinity of QRS-wave. For example, n2 is at the input time point n=3. The QRS-wave ends at the time point n2.

The variable tap coefficients in the FIR filter 22 initially have the first tap coefficients (a0, a1, a2) (see FIG. 5), which are suited for cutting off environmental noise (e.g. 20 Hz component of air-conditioning noise) from magnetocardiographic QRS-wave (0 to 50 Hz) (see FIG. 4 (b)).

The variable tap coefficients recorded in the respective multipliers 222p, 222q, 222r are then switched completely from the first tap coefficient (a2, a1, a0) to the second tap coefficient (b2, b1, b0) at the time point n=3 (see FIG. 6).

The variable tap coefficients are then switched gradually from the first tap coefficient (a0, a1, a2) to the second tap coefficient (b0, b1, b2) such that the FIR filter 22 outputs y[3]=b0x[3]+a1x[2]+a2x[1] (variable tap coefficients b0, a1, a2; see FIG. 6), the FIR filter 22 outputs y[4]=b0x[4]+b1x[3]+a2x[2] (variable tap coefficients b0, b1, a2; see FIG. 7), and then the FIR filter 22 outputs y[5]=b0x[5]+b1x[4]+b2x[3] (variable tap coefficients b0, b1, b2; see FIG. 8).

The variable tap coefficients in the FIR filter 22 are thus switched to the second tap coefficients (b0, b1, b2) (see FIG. 8), which are suited for cutting off environmental noise (e.g. 20 Hz component of air-conditioning noise) from magnetocardiographic T-wave (0 to 10 Hz) (see FIG. 4 (b)).

In accordance with the second embodiment, it is possible to smoothly switch the characteristics of the low-pass filter (FIR filter 22) during denoising (e.g. removal of environmental noise from magnetocardiographic and other measurement results).

Variation

It is noted that the FIR filter 22 may not be a transposed FIR filter as long as the first tap coefficients (a0, a1, a2) can be switched in the order of a0, a1, and a2 to the second tap coefficients (b0, b1, b2), though has been described as a transposed FIR filter in the second embodiment. For example, the FIR filter 22 may be a direct FIR filter.

The configuration of the FIR filter 22 according to the variation of the second embodiment is identical to that of the variation of the first embodiment (see FIGS. 9 to 12) and will not be described. Note here that the first tap coefficients (a0, a1, a2) are arranged to cause the FIR filter 22 to serve as a low-pass filter with the cut-off frequency set at a first frequency (50 Hz), as is the case in the second embodiment. On the other hand, the second tap coefficients (b0, b1, b2) are arranged to cause the FIR filter 22 to serve as a low-pass filter with the cut-off frequency set at a second frequency (20 Hz).

Incidentally, the above-described embodiments may be achieved as follows. A computer including a CPU, a hard disk, and a medium (USB memory, CD-ROM, or the like) reading device is caused to read a medium with a program recorded thereon that achieves the above-described components (e.g. the FIR filter 22, the replacement time point specifying section 24) and install the program in the hard disk. The above-described features can also be achieved in this manner.

DESCRIPTION OF REFERENCE NUMERAL

10 Magnetic Sensor Group
20 Filtering Apparatus
22 FIR Filter
220 Delay Summing Section
224p, 224q Delayers
226q, 226r Adders
222p, 222q, 222r Multipliers
227q, 227r Delaying Sections
228q, 228r Adders (Summing Section)
24 Replacement Time Point Specifying Section
242 Average Value Deriving Section
244 Variance Value Deriving Section
246 Local Minimum Time Point Deriving Section
D1 to D25 Magnetic Sensors
n Input Time Point (Sampling Time Point)
D1(n), D2(n), . . . , D24(n), D25(n) Input Digital Data
D(n)ave Average Value
V(n) Variance Value
n1 Time Point when QRS-wave starts
n2 Time Point when QRS-wave ends
a0, a1, a2 First Tap Coefficients
b0, b1, b2 Second Tap Coefficients

The invention claimed is:

1. A filtering apparatus comprising an FIR filter that has multipliers arranged to multiply input digital data having their respective different input time points by respective variable tap coefficients, wherein
the variable tap coefficients are each switched from a first tap coefficient to a second tap coefficient sequentially for the input digital data from later to earlier input time points,
the first tap coefficient is arranged to cause the FIR filter to serve as a low-pass filter with the cut-off frequency set at a first frequency,
the second tap coefficient is arranged to cause the FIR filter to serve as a low-pass filter with the cut-off frequency set at a second frequency different from the first frequency, and
the variable tap coefficients are switched for each multiplication by one of the multipliers.

2. The filtering apparatus according to claim 1, further comprising a delay summing section arranged to sum outputs from the multipliers while delaying to the input time point of the latest input digital data.

3. The filtering apparatus according to claim 2, wherein
the variable tap coefficients are recorded in the respective multipliers, and
the variable tap coefficients recorded in the respective multipliers are each switched completely from the first tap coefficient to the second tap coefficient at a predetermined time point.

4. The filtering apparatus according to claim 1, further comprising:
a delaying section arranged to delay inputs into the multipliers to the input time point of the latest input digital data; and
a summing section arranged to sum outputs from the multipliers.

5. The filtering apparatus according to claim 1, wherein the first frequency is lower than the second frequency.

6. The filtering apparatus according to claim 5, wherein the input digital data include data representing magnetocardiographic P-wave and QRS-wave.

7. The filtering apparatus according to claim 6, wherein the variable tap coefficients start to be switched at the time point when the QRS-wave starts in the magnetocardiographic waveform.

8. The filtering apparatus according to claim 7, wherein
the input digital data are acquired by a plurality of magnetocardiographic sensors, and
the QRS-wave starts at the time point when the square average of the differences between outputs from the plurality of magnetocardiographic sensors and the average value thereof reaches the first local minimum value in the vicinity of the QRS-wave.

9. The filtering apparatus according to claim 1, wherein the first frequency is higher than the second frequency.

10. The filtering apparatus according to claim 9, wherein the input digital data include data representing magnetocardiographic P-wave, QRS-wave, and T-wave.

11. The filtering apparatus according to claim 10, wherein the variable tap coefficients start to be switched at the time point when the QRS-wave ends in the magnetocardiographic waveform.

12. The filtering apparatus according to claim 11, wherein
the input digital data are acquired by a plurality of magnetocardiographic sensors, and
the QRS-wave ends at the time point when the square average of the differences between outputs from the plurality of magnetocardiographic sensors and the average value thereof reaches the second local minimum value in the vicinity of the QRS-wave.

13. A filtering method with using an FIR filter that has multipliers arranged to multiply input digital data having their respective different input time points by respective variable tap coefficients, the filtering method comprising:
switching the respective variable tap coefficients from a first tap coefficient to a second tap coefficient sequentially for the input digital data from later to earlier input time points, wherein
the first tap coefficient is arranged to cause the FIR filter to serve as a low-pass filter with the cut-off frequency set at a first frequency,
the second tap coefficient is arranged to cause the FIR filter to serve as a low-pass filter with the cut-off frequency set at a second frequency different from the first frequency, and
the variable tap coefficients are switched for each multiplication by one of the multipliers.

14. A non-transitory computer-readable medium including a program of instructions for execution by a computer to perform a filtering process with using an FIR filter that has multipliers arranged to multiply input digital data having their respective different input time points by respective variable tap coefficients, the filtering process comprising:
switching the respective variable tap coefficients from a first tap coefficient to a second tap coefficient sequentially for the input digital data from later to earlier input time points, wherein
the first tap coefficient is arranged to cause the FIR filter to serve as a low-pass filter with the cut-off frequency set at a first frequency,
the second tap coefficient is arranged to cause the FIR filter to serve as a low-pass filter with the cut-off frequency set at a second frequency different from the first frequency, and
the variable tap coefficients are switched for each multiplication by one of the multipliers.

* * * * *